United States Patent [19]

Marshall

[11] Patent Number: 4,873,997
[45] Date of Patent: Oct. 17, 1989

[54] SURGICAL DRAPE

[75] Inventor: Lyman R. Marshall, Asheville, N.C.

[73] Assignee: Scherer Healthcare Ltd., Asheville, N.C.

[21] Appl. No.: 186,099

[22] Filed: Apr. 25, 1988

[51] Int. Cl.⁴ ............................................. A61F 13/00
[52] U.S. Cl. ..................................... 128/849; 128/853; 128/855
[58] Field of Search ............... 128/132 D, 132 R, 849, 128/853, 854, 855; 5/45, 46, 494

[56] References Cited

U.S. PATENT DOCUMENTS

| | | | |
|---|---|---|---|
| 3,377,636 | 4/1968 | Addario | 5/499 |
| 3,921,627 | 11/1975 | Wilson et al. | 128/132 D |
| 4,275,720 | 6/1981 | Wichman | 128/853 |
| 4,316,455 | 2/1982 | Stoneback | 128/132 D |
| 4,414,968 | 11/1983 | Amin | 128/132 D |
| 4,745,915 | 5/1988 | Enright et al. | 128/132 D |

Primary Examiner—Robert A. Hafer
Assistant Examiner—Michael Brown
Attorney, Agent, or Firm—David M. Carter

[57] ABSTRACT

There is provided an improved surgical drape with a central sheet having at least one hole therein through which surgical procedure is to be performed. A pair of elongated pleats are formed in the central sheet along its outer edge, providing barriers to fluid which runs off from the site of surgical procedure and further directing the fluid along a portion of the central sheet so that fluid is more readily absorbed or contained. A pair of plastic sheets are connected to the central sheet on either side of the pleats.

2 Claims, 1 Drawing Sheet

SURGICAL DRAPE

BACKGROUND OF THE INVENTION

This invention relates to apparatus used in connection with surgical procedures. More particularly it relates to improved surgical drapes for absorbing and/or containing fluid runoff from the site of surgical procedure.

In the course of performing surgery, large drapes are commonly used to cover a major portion of the patient. The drape normally includes a hole therein which provides access to the site of surgical procedure. Surgical drapes perform the dual function of maintaining a sterile field about the surgical procedure site and also absorbing and containing fluid runoff which normally occurs at the site of the procedure. It is undesirable for bodily fluids which leave the site of surgical procedure to fall on the floor of the operating room for reasons of sterility and appearance, and because the fluids may be tracked out of the room and the floor is made slippery. The problem has become more acute with the advent of the AIDS virus.

There have been recent improvements in surgical drapes to deal with the problem of spillage of bodily fluids onto the floor. Several of these improvements are shown in U.S. Pat. Nos. 3,791,382, and 4,378,794, both assigned to the Kendall Corporation. The Kendall patents provide for the use of pockets which are attached to the drape for catching the fluid as it runs off the drape. One of the drawbacks to the Kendall drapes is that it is rather expensive to manufacture since a pocket must be added. Furthermore, the entire Kendall drape is made of a thick material which also adds to the expense.

Other prior art surgical drapes are shown in U.S. Pat. Nos. 4,524,767, 4,316,456, 4,336,797, and 3,926,185.

In the early 1970s a change from reusable linen to disposable surgical drapes began. Today the vast majority of surgical drapes are disposable. They provide not only cost saving factors to a hospital but also help in operating room technique and improve infection control.

Many of the small surgical drapes such as underbuttocks drapes, half sheets, three quarter sheets, and small procedure drapes have been automated with price reductions passed to the medical market.

The large procedure drapes are still made by hand labor operations and have not shown corresponding price reductions as the automated drapes have. It is therefore desirable to automatically produce disposable large procedure drapes which provide better control of bodily fluids.

OBJECTS OF THE INVENTION

It is therefore one object of this invention to provide an improved surgical drape.

It is another object to provide a surgical drape which will adequately absorb and/or contain body fluids but is inexpensive to produce.

It is still another object to provide a large procedure disposable drape which may be automatically produced and which controls bodily fluids.

SUMMARY OF THE INVENTION

In accordance with one form of this invention there is provided an improved surgical drape including a first sheet for receiving fluid runoff from a site of surgical procedure. A mechanism is provided for directing the fluid flow along a portion of the first sheet. The fluid directing mechanism is connected to the first sheet and may be formed as a part of the first sheet. At least a second sheet is connected to the first sheet. Preferably the second sheet or sheets are connected on either side of the mechanism for directing the fluid flow. Also, preferably the second sheet or sheets are made of inexpensive material such as, for example, plastic.

In another form of Applicant's invention, there is provided an improved surgical drape including an absorbent sheet for receiving fluid runoff from the site of surgical procedure. A pair of substantially parallel elongated pleats extend upwardly from the absorbent sheet. The pleats form barriers to the fluid and further direct the flow of the fluid. Thus the fluid will be spread out and be more readily absorbed and/or contained by the absorbent sheet. Preferably the pleats run near two of the outer edges of the absorbent sheet and are connected to at least one inexpensive sheet forming the remainder of the drape.

BRIEF DESCRIPTION OF THE DRAWINGS

The subject matter which is regarded as the invention is set forth in the appended claims. The invention itself, together with further objects and advantages thereof, may be better understood by reference to the following descriptions taken in conjunction with the accompanying drawings in which;

DESCRIPTION OF THE PREFERRED EMBODIMENT

Figure 1:
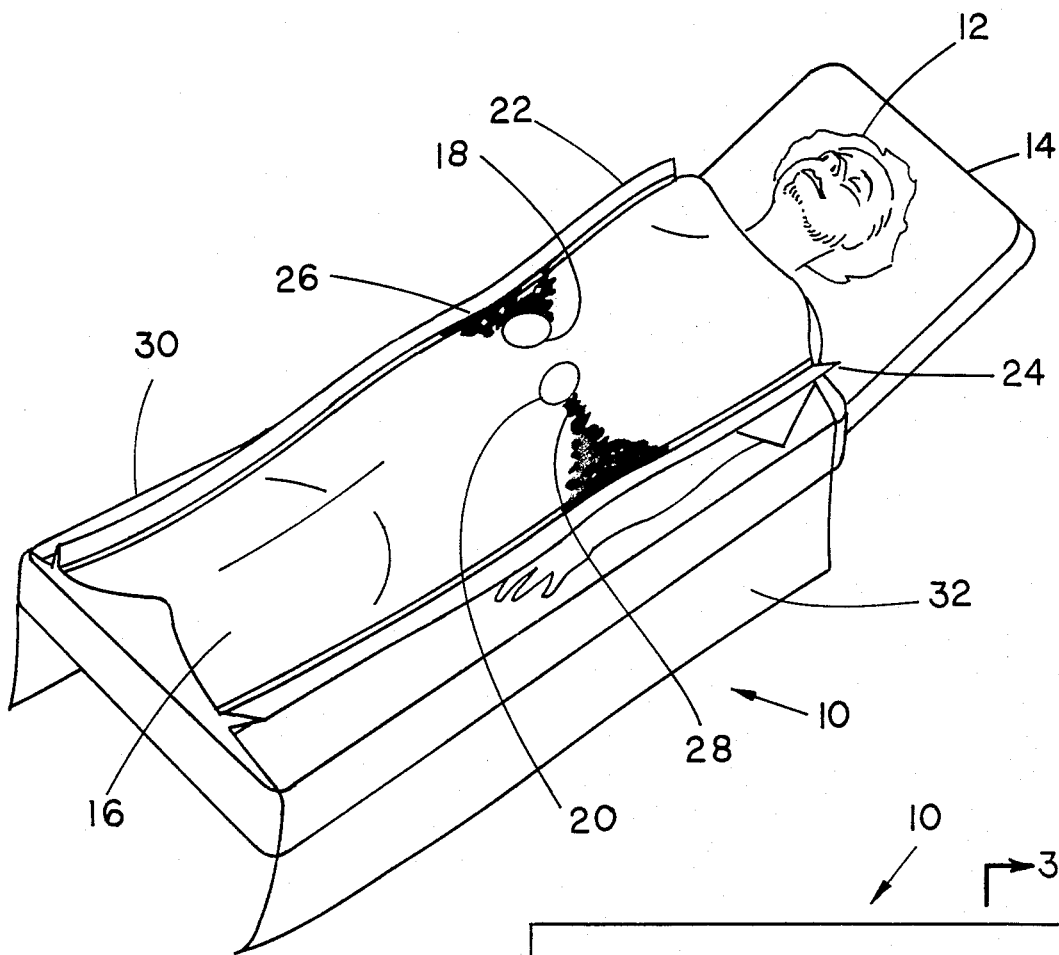
FIG. 1 is a pictorial view showing a surgical drape of the subject invention covering a patient.
Figure 2:
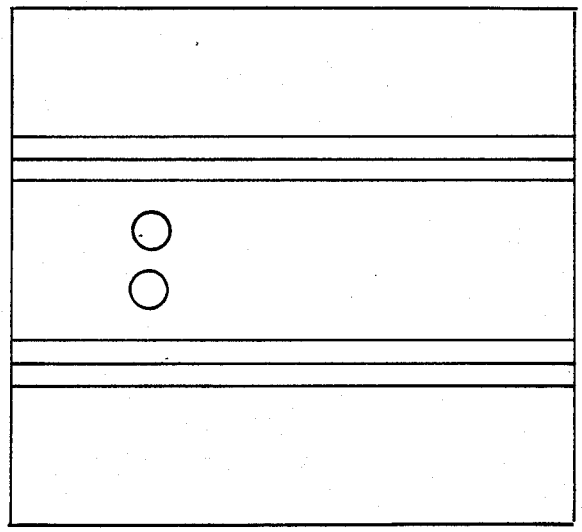
FIG. 2 is a plan view of the surgical drape shown in FIG. 1.

Referring now more particularly to FIG. 1, there is provided surgical drape 10 covering patient 12 who is resting on operating table 14. Surgical drape 10 includes a central sheet 16 which is preferably primarily made of a fibrous fluid absorbent material such as, for example, cotton or rayon. The fibrous absorbent material may be covered with a thin fluid permeable cover.

Central sheet 16 includes at least one hole therein to provide access for the surgeon at the surgical site. The position and shape of the hole or holes is specifically designed for each surgical procedure. The drape shown in FIG. 1 includes holes 18 and 20. The drape of the exemplification embodiment is used for an abdominal surgical procedure.

The central sheet includes a pair of pleats 22 and 24 formed therein. Preferably the pleats 22 and 24 extend along the outer edge of central sheet 16 and rise upwardly. As can be seen, bodily fluids 26 and 28, such as blood and the like, come from holes 18 and 20 during surgery. The upright pleats 22 and 24 form barriers against the bodily fluids and also direct the bodily fluids along the elongated directions of the pleats, thus spreading the bodily fluids around a substantially much larger area on the contral sheet than if the pleats were not in place. Thus the fluid is contained better and, if the central sheet is absorbent, more of the fluid will be absorbed. By utilizing these pleats, it is believed that a bag is no longer necessary to catch fluids, in most cases, in order to keep the fluids from spilling onto the floor. Furthermore, because the fluid is spread out, a smaller amount of the more expensive central sheet material is needed. Also, because the pleats form barriers, the fluid cannot easily run off the sides of the drape.

Figure 3:
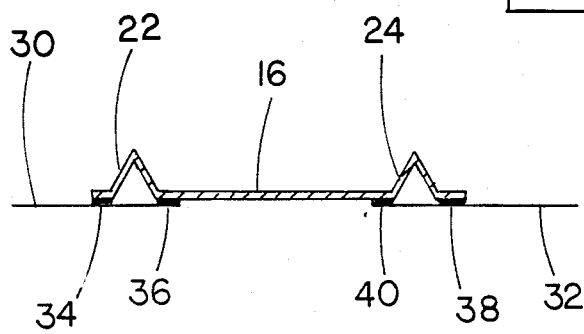
FIG. 3 is a sectional view of the drape of FIG. 2 taken along section line 3—3.

Clear plastic sheets 30 and 32 are connected to the central sheet along their outer edges at the bottom of the pleats and form the sides of the drape. This may be better seen in reference to FIG. 3. Clear plastic sheet 30 is sealed or glued to the bottom of pleat 22 at positions 34 and 36. Clear plastic sheet 32 is sealed or glued to the bottom of pleat 24 at positions 38 and 40. By sealing or gluing the clear plastic sheets to the bottom of the pleats, the pleats will maintain their triangular shape and will remain in an upright position to act as a fluid barrier and fluid direction flow mechanism. Furthermore, the clear plastic sheets 30 and 32 are much less expensive than the central sheet 16, thus reducing the overall cost of the drape. Also, since it is preferable that the plastic sheets 30 and 32 be clear, the surgeon is able to more easily view certain portions of the patient and is able to see other things which may have been placed on the operating table under the drape. Most prior drapes are made of a single opaque sheet of material and thus the surgeon cannot see any substantial part of the patient other than what is viewed through the holes at the operation site and normally cannot see the part of the table which is covered.

From the foregoing description of the preferred embodiment of the invention, it will be apparent that many modifications may be made therein without departing from the true spirit and scope of the invention and this invention is not limited thereto.

I claim:

1. An improved surgical drape comprising: a first sheet for receiving fluid runoff from a site of surgical procedure; means for directing the fluid along a portion of said first sheet; said means for directing located on said first sheet; at least a second sheet connected to said first sheet; a third sheet; said first sheet being located between said second and third sheets; said means for directing includes first and second pleats; said second sheet connected to said first pleat and said third sheet connected to said second pleat.

2. A drape as set forth in claim 1 wherein each of said pleats is held in a substantially upright position by the adherence of portions of said second and third sheets to the bottom of its respective pleat.

* * * * *